United States Patent [19]
Wohlwend

[11] Patent Number: 5,788,498
[45] Date of Patent: Aug. 4, 1998

[54] METHOD FOR MANUFACTURING DENTAL CROWNS

[75] Inventor: Arnold Wohlwend, Zürich, Switzerland

[73] Assignee: Ivoclar AG, Schaun, Liechtenstein

[21] Appl. No.: 768,957

[22] Filed: Dec. 18, 1996

[30] Foreign Application Priority Data

Dec. 19, 1995 [CH] Switzerland ............ 03375/95

[51] Int. Cl.⁶ ...................................................... A61C 5/10
[52] U.S. Cl. ........................ 433/223; 433/215; 433/218; 264/19
[58] Field of Search .................................. 433/167, 171, 433/180, 181, 182, 190, 191, 218, 223; 264/19

[56] References Cited

U.S. PATENT DOCUMENTS

| | | |
|---|---|---|
| 1,688,621 | 10/1928 | Huber ............................. 433/180 |
| 3,530,582 | 9/1970 | Weissman ........................ 433/191 |
| 4,661,067 | 4/1987 | Harvey, Sr. et al. ............ 433/180 |
| 4,740,160 | 4/1988 | Hruska ............................ 433/181 |
| 4,741,699 | 5/1988 | Kosmos ........................ 433/203.1 |
| 4,744,757 | 5/1988 | Adair et al. ..................... 433/180 |
| 4,971,558 | 11/1990 | Jacobi ............................ 433/226 |
| 5,064,731 | 11/1991 | Miyazaki et al. ............... 433/207 |
| 5,106,303 | 4/1992 | Oden et al. ..................... 433/223 |
| 5,217,375 | 6/1993 | Oden et al. ..................... 433/218 |
| 5,342,201 | 8/1994 | Oden ............................... 433/218 |
| 5,614,330 | 3/1997 | Panzera et al. ................. 433/206 |

FOREIGN PATENT DOCUMENTS

| | | |
|---|---|---|
| 0 231 773 | 8/1987 | European Pat. Off. . |
| 664 133 | 8/1938 | Germany . |
| 31 34 484 | 3/1983 | Germany . |
| G 84 37 158 | 3/1985 | Germany . |
| 36 05 437 | 8/1987 | Germany . |
| 094008783 | 4/1994 | WIPO ...................... 433/180 |

*Primary Examiner*—John J. Wilson
*Attorney, Agent, or Firm*—John C. Thompson; Alan S. Korman

[57] ABSTRACT

A method for manufacturing an artificial tooth replacement for at least one tooth includes the step of prefabricating a ceramic reinforcement member. Connecting elements are formed at the reinforcement member for fastening the artificial tooth replacement to at least one tooth stump of a patient. The ceramic reinforcement member is covered with a ceramic cover material for completing the artificial tooth replacement.

26 Claims, 3 Drawing Sheets

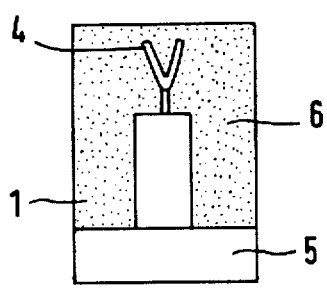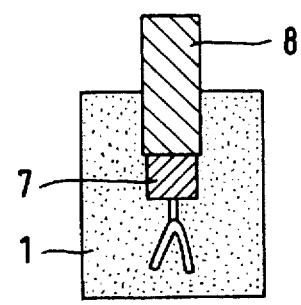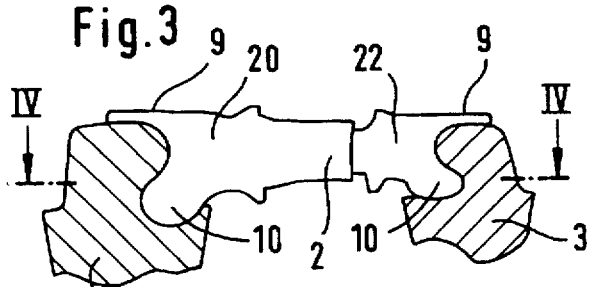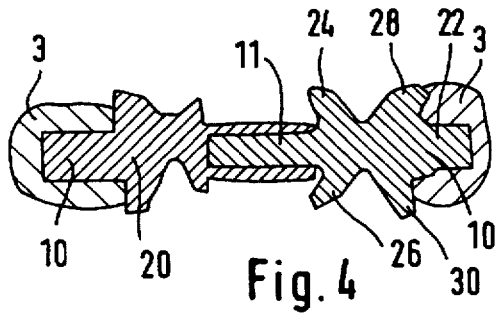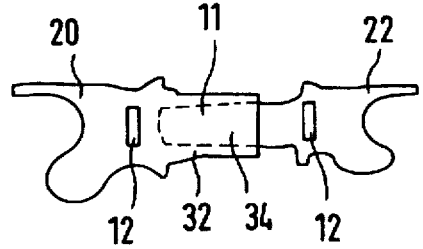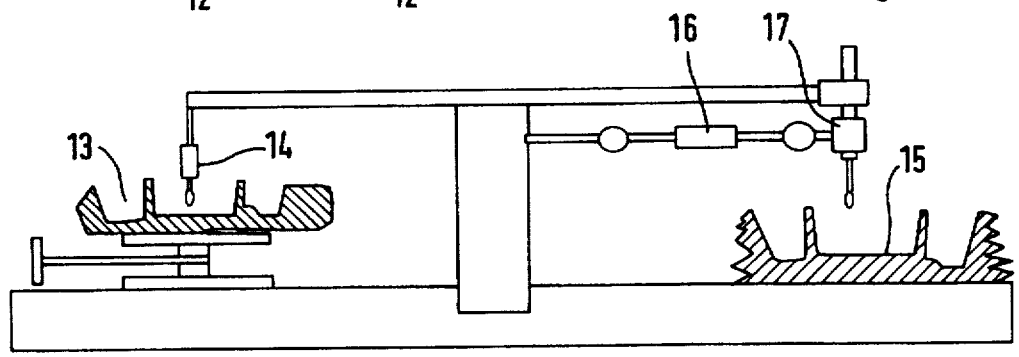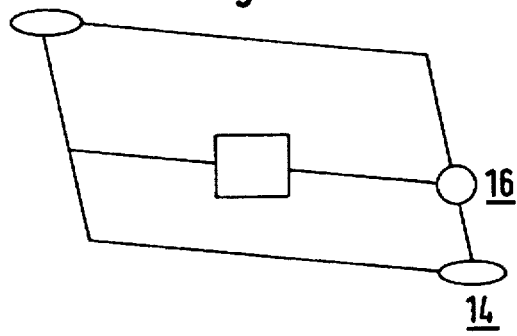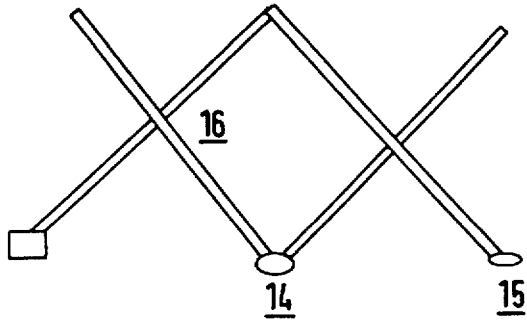

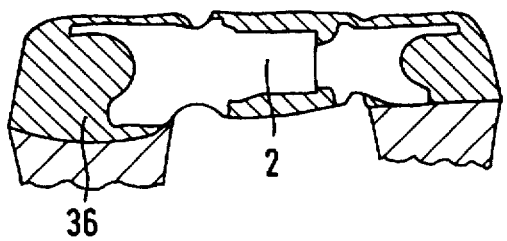
Fig.9
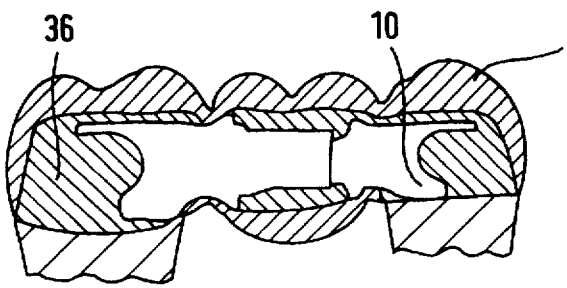
Fig.10
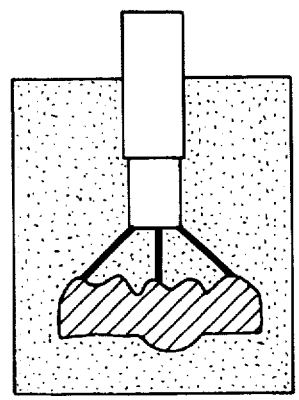
Fig.11
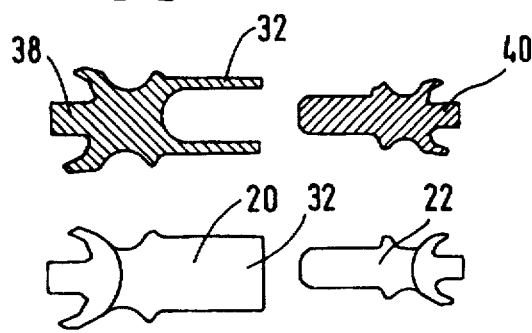
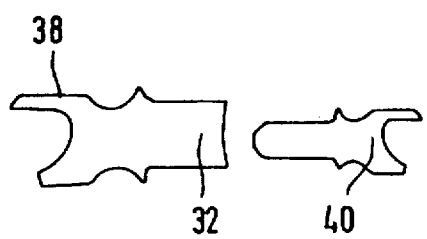
Fig.12    Fig.13
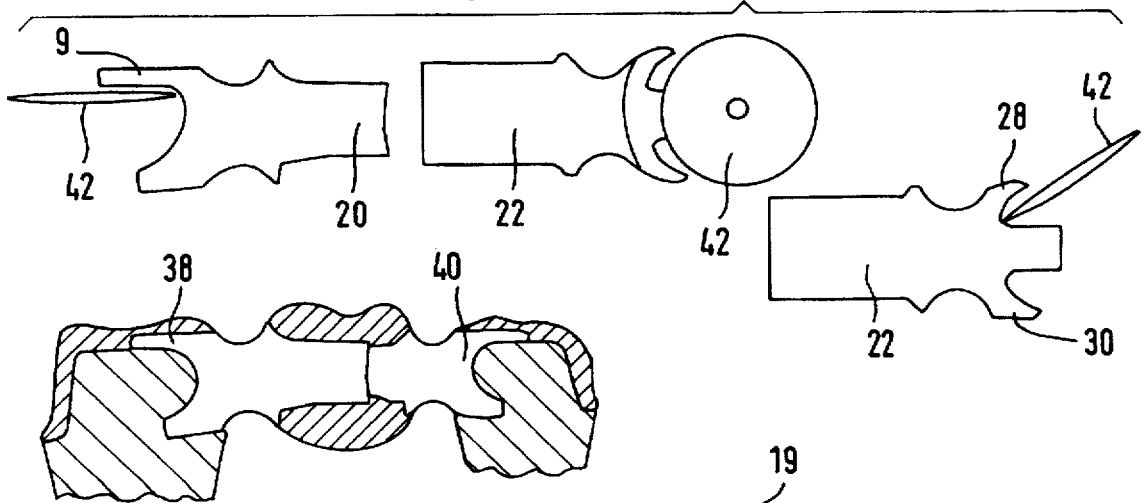
Fig.14
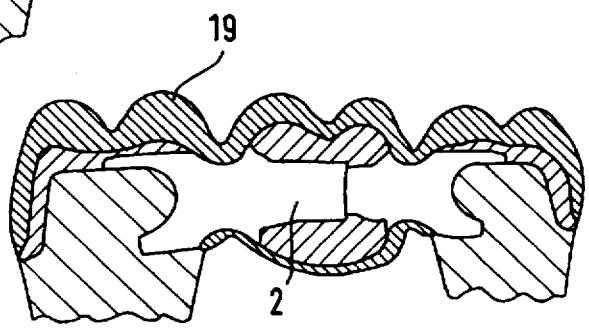
Fig.15

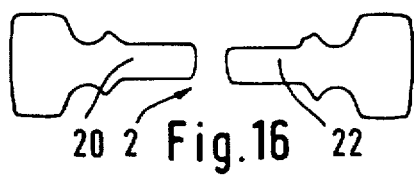
Fig. 16
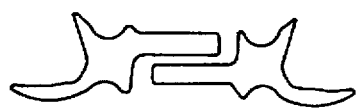
Fig. 17
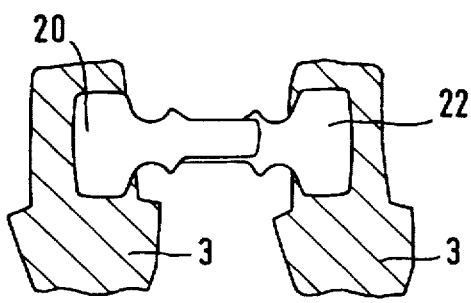
Fig. 18
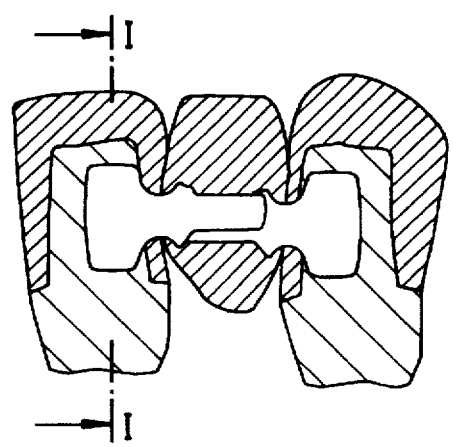
Fig. 19
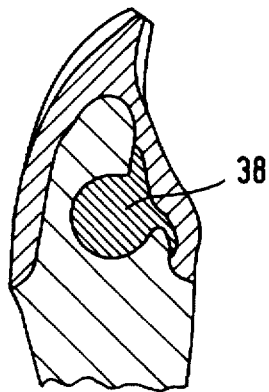
Fig. 20
  
Fig. 21
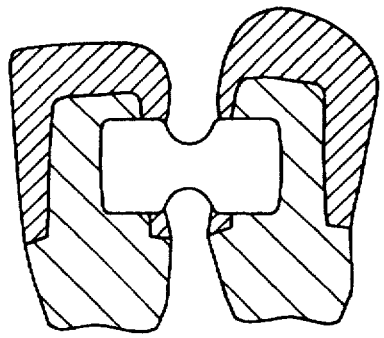
Fig. 22

METHOD FOR MANUFACTURING DENTAL CROWNS

BACKGROUND OF THE INVENTION

The present invention relates to a method for manufacturing artificial tooth replacements such as dental crowns and/or dental bridges, especially with a slide connection for bridge members, whereby connectors or retention parts are connected to at least one tooth stump or stub and covered by a ceramic material.

Such a method is known from German published document 36 05 437. This document teaches to manufacture mechanically highly loaded parts of an artificial tooth replacement from a dental casting material and to manufacture other portions of a ceramic material. According to this document a ceramic crown according to the jacket crown technique is to be replaced by a crown made of dental casting material, i.e., by a crown made according to the metal/ceramic technique. The dental casting material is then to be covered with a ceramic material and, for this purpose, dental casting materials that can be fired and have a thermal expansion coefficient that is adjusted to the ceramic cover material are to be used.

This known method however has not found acceptance in dentistry. Even when the deviations between the thermal expansion coefficient of the ceramic cover material of, for example, 9.5 μm/m°K and a suitable dental casting material matched closely, during sintering stress fractures within the dental ceramic material occur frequently which during the course of time will result in the ceramic cover material flaking off. This is especially critical when thin cover materials, for example, of a wall thickness of 0.5 to 1 mm are used because then the stress fractures always result in a weakening of the ceramic material and will cause chipping or flaking.

In order to keep the loss of tooth substance as small as possible, it is known to use bridge members with a slide connection. The bridge members are thus slidable and optionally also rotationally movable relative to one another before the ceramic cover material is sintered thereon. With such a slide connection the connectors for connecting the tooth replacement to the tooth material can be formed in a manner known per se in a pawl-like construction so that an especially good anchoring is ensured. Such a slide connection is especially suitable for manufacturing bridges for molars across a tooth gap of more than one molar and can also be used for bridging incisors. An example for a dental bridge of a great length is known from German Gebrauchsmuster 84 37 158. This dental bridge comprises a sliding connection preferably made of non-ferrous or ferrous metal wire.

Furthermore, from German published document 31 34 484 a slide connection is known in which the bridge members are comprised of a platinum/gold alloy. It is understood that instead of this alloy other dental casting materials of suitable alloys can be used.

In addition to the known aesthetic problems due to the insufficient transmission properties of the metal ceramic composite for light there is furthermore a problem in such metal ceramic composite slide connections that with increasing age of the patient the gums will shrink so that the metallic base will be visible.

In order to provide a translucent character to the thin ceramic cover material of the metal ceramic composite it is known to coat the metal structure with a so-called opacity-inparting agent. Thus, such a metal ceramic composite is comprised of three layers of potentially different thermal expansion coefficients, and this will exacerbate the aforementioned problem.

It is therefore an object of the present invention to provide a method of the aforementioned kind with which, over an extended service life, an aesthetically satisfying result especially for incisor bridges as well as molar bridges is possible.

SUMMARY OF THE INVENTION

The method for manufacturing an artificial tooth replacement for at least one tooth according to the present invention is primarily characterized by:

Prefabricating a ceramic reinforcement member;

Forming connecting elements at the ceramic reinforcement member for fastening the artificial tooth replacement to at least one tooth stump of a patient; and Covering the ceramic reinforcement member with a ceramic cover material for completing the artificial tooth replacement.

Preferably, the ceramic reinforcement member is comprised of an oxide ceramic and the step of prefabricating includes sintering the oxide ceramic by hot pressing.

The oxide ceramic is comprised of at least 90% of at least one oxide selected from the group consisting of sirconium oxide and aluminum oxide and 0% to 10% of at least one oxide selected from the group consisting of atrium oxide, calcium oxide, and magnesium oxide.

Expediently, the ceramic material has a lesser hardness than the ceramic reinforcement member, wherein the ceramic cover material is at least partially comprised of feldspar ceramic, wherein the step of covering includes the step of fusing the feldspar ceramic to the ceramic reinforcement member by ceramic hot-pressing.

The step of prefabricating includes preferably producing bridge members and a slide connection, for slidably connecting the bridge members, as parts of the ceramic reinforcement member.

The slide connection has a force-transmitting portion that is entirely a part of the ceramic reinforcement member.

Preferably, the ceramic reinforcement member is comprised of a ceramic selected from the group consisting of silicon nitride, boronitride, and a ceramic having a flexural strength of more than 700 MPa.

The step of prefabricating may include the step of presintering the ceramic reinforcement member, preparing, on an enlarged scale relative to an imprint of a tooth stump of a patient, a receiving opening of the ceramic reinforcement member for receiving the tooth stump with the aid of a pantograph, and finish-sintering the ceramic reinforcement member.

The step of prefabricating may also include finish-sintering the ceramic reinforcement member and subsequently preparing a receiving opening of the reinforcement member for receiving a tooth stump with the aid of a copying and grinding machine that senses with one machine tool an imprint of a tooth stump of a patient and grinds with another machine tool the receiving opening accordingly.

Expediently, the method further comprises the step of providing one of the connecting elements with a hole and, in the step of covering the hole is filled with ceramic cover material by hot-pressing.

In the step of prefabricating the reinforcement member is preferably prepared as an oversized ceramic blank. A receiving opening, having a shape matching a tooth stump of a patient, is milled with the aid of a pantograph into the ceramic blank, Subsequently, the milled ceramic blank is finish-sintered.

Advantageously, the step of covering includes the steps of firing and hot-pressing a plurality of differently colored meltable ceramics, in the form of raw material, onto the reinforcement member by hot-pressing method.

The method preferably further includes applying a ceramic support structure onto the reinforcement member, the ceramic support structure comprised at least partially of the same ceramic material as the ceramic reinforcement member, wherein in the step of covering the ceramic cover material is selected from the group consisting of glass, zirconium containing glass, and feldspar.

In the step of covering the ceramic reinforcement member is preferably completely covered with the ceramic cover material and is designed to engage two tooth stumps of a patient to form a dental bridge.

The step of covering may include selecting the ceramic cover material to have a thermal expansion coefficient identical to the thermal expansion coefficient of the ceramic reinforcement member comprised of zirconium oxide ceramic.

The step of covering may include selecting the ceramic cover material to be comprised of 20% to 40% by weight of a ceramic selected from the group consisting of glass ceramic and feldspar ceramic and 60% to 80% by weight of zirconium oxide.

The step of forming may include imparting to a portion of the connecting element, facing a tooth stump of a patient, a shape suitable for grinding with a grinding wheel and providing the connecting element with a claw facing the tooth stump, wherein the surface of the claw facing the tooth stump is ground to form an abutment for the tooth stump.

The step of forming may include imparting to a portion of the connecting element, facing the tooth stump of a patient, a shape with multiple fingers suitable for grinding with a grinding wheel. The fingers may be arranged as to diverge or so as to be star-shaped.

The step of prefabricating includes producing bridge members as parts of the reinforcement member and a slide connection for slidably connecting the bridge members, wherein the slide connection comprises a pin and a sleeve.

The step of prefabricating comprises producing bridge members as parts of the reinforcement member and a slight connection for slidably connecting the bridge members. The slight connection may comprise two pins extending adjacent to one another in a common plane.

The reinforcement member is preferably a connector between two adjacent teeth of a patient, wherein the step of prefabricating includes providing fastening flaps to be positioned at an inwardly facing side of the teeth and providing a constriction in an area between the teeth.

The method may include molding onto the reinforcement member a support structure blank of a light-curing plastic material, subsequently embedding the reinforcement member with support structure blank, in a mold, and replacing the light-curing plastic material with a support ceramic material to form a ceramic support structure. The subsequent step of covering includes hot-pressing the ceramic cover material onto the ceramic reinforcement member.

The step of prefabricating may also include using a metal for the reinforcement member and the step of covering them includes applying an opacity-imparting substance.

The step of covering may further include painting a ceramic paint onto the opacity-imparting substance in order to produce a desired color of the artificial tooth replacement.

Surprisingly, the inventive measure, i.e., using a ceramic reinforcement member as a reinforcement of the artificial tooth replacement, overcomes the aforementioned problem.

The thermal expansion coefficient can be precisely adjusted in accordance with the used ceramic material. A shrinkage of the gums does not result, even for very long dental bridge constructions, in metal parts becoming exposed and visible which is an unaesthetical sight. An opacity-imparting layer is obsolete so that the manufacturing costs are reduced.

The inventive ceramic reinforcement member can be expediently produced by hot-pressing whereby it is understood that, after correspondingly shaping the ceramic reinforcement member the ceramic cover material, which, for example, is comprised of glass ceramic or feldspar ceramic, can be sintered onto the ceramic reinforcement member comprised of a zirconium oxide ceramic or aluminum oxide ceramic.

A further advantage of the inventive method is the possibility to monitor the tooth situation by x-ray examination. This possibility is especially favorable in connection with crowns. The inventive ceramic system provides an increased light transmission, similar to that of a natural tooth comprised of a dentin core to which to the ceramic reinforcement member corresponds and the tooth enamel to which the sintered ceramic cover material corresponds.

The inventive construction of a dental crown or a dental bridge is thus similar to that of a natural tooth so that an optimal reproduction is possible.

It is especially advantageous that the rather hard ceramic reinforcement member is prefabricated, be it in the form of a slide connection or as a support structure for crowning. Thus, it is not required that the individual dental lab or the individual dentist purchase expensive CAD/CAM systems with which a three-dimensional machining is possible.

Inventively, a one-dimensional, at most a two-dimensional, machining is possible which can be easily carried out with a pantograph-like device.

According to a further inventive embodiment, it is suggested that the force transmission of the chewing forces via the dental bridge, respectively, dental crowns to the tooth stumps be effected primarily with the ceramic reinforcement member especially with respect to tensile load.

The ceramic cover material thus serves only as a means for pressure transmission from the chewing surface onto the ceramic reinforcement member and is thus not loaded by tensile and shearing loads. Accordingly, it is not detrimental that it has a low flexural strength of, for example, only 200 to 400 MPa since the very stable ceramic material of the reinforcement member acting as a reinforcement structure provides a flexural strength of, for example, 800 to 1500 MPa, preferably approximately 1200 MPa. In this context it is especially favorable that the softer ceramic material can be machined more easily and is adaptable and moldable to the desired shape.

Inventively, the ceramic reinforcement member also serves as a reinforcement during grinding processes. Even for very thin edge portions, the stiffening effect of the reinforcement member reduces the tendency of fracturing so that post machining by grinding is less critical.

BRIEF DESCRIPTION OF THE DRAWINGS

The object and advantages of the present invention will appear more clearly from the following specification in conjunction with the accompanying drawings, in which:

FIG. 1 shows a preparative step of the inventive method in a schematic representation of the hot-pressing method in a muffle furnace;

FIG. 2 shows a schematic view of a further step of the hot-pressing method in a muffle furnace;

FIG. 3 shows a representation of an embodiment of the inventive reinforcement member comprising a slide connection, FIG. 4 shows a schematic horizontal section of a slide connection of FIG. 3;

FIG. 5 is a further embodiment of an inventive reinforcement member in a side view;

FIG. 6 shows a representation of a pantograph-like device in a side view;

FIG. 7 shows a schematic view of a pantograph for manufacturing an enlarged receiving opening in a top view;

FIG. 8 shows a modified embodiment of the pantograph-like device in a schematic representation;

FIG. 9 shows a side view of a support structure prepared according to the inventive method, showing the hollow space in the mold filled with wax to be replaced by feldspar ceramic or glass ceramic;

FIG. 10 shows the support structure of FIG. 9 the outer shape of which is modeled in wax;

FIG. 11 shoves the method step of embedding the structure of FIG. 10 into a muffle furnace for performing the hot-pressing method;

FIG. 12 is a representation of an embodiment of the inventive reinforcement member comprised of two bridge members for the molar areas in a top view, bottom view, and side view:

FIG. 13 is a representation of a bridge member that is to be ground, in a view from the side, from below and from the top;

FIG. 14 is a representation of the support structure with hotpressed ceramic material;

FIG. 15 is a representation of the support structure of FIG. 14 with ceramic cover material that is hot-pressed or applied in powder form;

FIG. 16 is a view of two bridge members for the incisor area from behind;

FIG. 17 is a view of two bridge members for the incisor area according to FIG. 16 in a top view;

FIG. 18 shows the bridge members of FIG. 16 inserted into the incisor area;

FIG. 19 shows a view of a dental bridge manufactured according to the inventive method for the incisor area viewed from the palate;

FIG. 20 is a sectional view along the line 1—1 of FIG. 19 of an incisor with the mounted dental bridge;

FIG. 21 is a view of a connector from behind, from the top, and from the side, whereby the connector is inventively embodied as a ceramic reinforcement member; and FIG. 22 shows the connector of FIG. 21 after mounting for blocking two neighboring teeth.

DESCRIPTION OF PREFERRED EMBODIMENTS

The present invention will now be described in detail with the aid of several specific embodiments utilizing FIGS. 1 through 22.

FIG. 1 shows in a schematic representation a muffle furnace 1 for performing the IPS Empress method of the applicant. Details of the method can be taken from European application 231 773, the disclosure of which is hereby incorporated by reference.

The dentin structure is molded in wax onto a special support 5 and embedded in a material 6. According to FIG. 2 a ceramic blank 7 is introduced via an aluminum plug 8 into the muffle furnace which is heated to approximately 800° C.

Subsequently, heating to approximately 1150° C. is performed so that the ceramic blank 7 becomes flowable and conforms to the desired shape of the crown or dentin structure. Pressure applied via the aluminum plug 8 ensures that the desired structure is achieved.

As can be seen in FIG. 3, a reinforcement member 2 as a reinforcement for the manufacture of a dental crown (not represented) in FIG. 3 is arranged between teeth 3. The reinforcement member 2 is comprised of two bridge members 20, 22 which are engaged with a slide connection 11 that is shown in more detail in FIG. 5. The bridge members 20 and 22 terminate in substantially pawl-shaped supports 9 which allow for a positive-locking engagement of the dentin of tooth 3. Due to the positive-locking engagement and the pawl-shaped projections 10 of the reinforcement member 2, the crown is securely and pull-resistantly connected to the teeth 3.

The inventive reinforcement member 2 consists of zirconium oxide ceramic mixed with 5% yttrium oxide with a mechanical strength of 900 to 1200 MPa and a tetragonal stabilized lattice structure. The bridge members 20, 22 can also be industrially prefabricated and can be finish-sintered in the shown embodiment.

The design of the bridge members with the slide connection 11 allows for an especially favorable force introduction for the transmission of forces from the chewing surface of the intermediate member, formed by the slide connection 11, onto the neighboring teeth.

FIG. 4 shows the inventive reinforcement member 2 in a horizontal section along the line IV—IV. It is shown that the bridge members 20, 22 have connecting elements in the form of projections 24, 26, 28 and 30 which are matched to the shape of the teeth. The pawl-shaped projections 24 and 26 are adapted to the exterior shape of the intermediate tooth to be modeled later on and the pawl-shaped projections 28 and 30 are adapted to the exterior shape of the neighboring tooth 3. The same holds true for the pawl-shaped projections of the bridge member 20.

As can be seen in FIG. 5, the slide connection 11 in the shown embodiment is provided with two securing stays 12 that during hot-pressing will prevent that the slide connection 11 is compressed. The slide connection 11 is comprised of a bushing or sleeve 32 and a pin 34 which engage one another in a manner known per se. A securing rod 12 is provided at each one of the two bridge members 20 and 22.

Preferably, a gap or recess is provided in the intermediate space between the sleeve 32 and the pin 34. This ensures that the intermediate space during hot-pressing is filled with the surrounding ceramic material so that the slide connection is stiffened (mechanically stabilized).

While the manufacture of an artificial tooth replacement according to FIGS. 1 through 5 is especially suitable for dental bridges, which are to bridge an intermediate tooth, it is also possible to inventively manufacture dental bridges comprised of a ceramic reinforcement member and extending over a great length.

In the most extreme cases the inventively manufactured bridges can extend over the entire length of the jaw.

Preferably, presintered reinforcement members are used for such purposes. By presintering it is possible to produce a presintered part in an enlarged state. For its machining the pantograph-like device represented in FIGS. 6 through 8 can be used.

Inventively, in this context it is especially advantageous that only a one-dimensional, at most a two-dimensional machining is required. In FIG. 6, a mold (impression) 13 of the ground tooth of a patient is fixedly mounted on a support. A contour sensor 14 glides along the inner portion of the mold and via a pantograph, represented in FIGS. 7 and 8 in more detail, the movement of the sensor 14 is transmitted onto a cutter 17 at an enlarged scale. The desired scale can be selected with a control member 16. A ceramic block 15 is thus milled according to the desired shape whereby the enlargement can be, for example, 10 to 30%.

The enlargement can be performed in a manner known per se via the shown pantograph linkage as represented in FIGS. 7 and 8.

The thus manufactured parts must be subsequently finish-sintered. In FIG. 9, in order to simplify the drawing, a reinforcement member for bridging only one intermediate tooth is represented. However, it is understood that this embodiment can be used also for larger bridges.

The outer shape is molded with wax 36 onto the finished support structure (reinforcement member) and the resulting shape with the exterior wax coating is embedded into the refractory material within the furnace and the furnace is heated to 900° C. The wax melts and leaves a hollow space.

The hollow space is then filled by hot-pressing with a feldspar ceramic or glass ceramic. Preferably, in this embodiment the feldspar ceramic or glass ceramic may contain about 20% oxide particles, especially zirconium oxide particles, whereby, depending on the required specifications, the oxide contents can be increased to 80%.

This ceramic material is already adapted with respect to color and translucence to the natural tooth dentin. The hot-pressing temperature of the hot-pressing method depends on the proportion of oxide particles and can be between 1000° and 1300°. The mechanical strength of the fired material depends also on the proportion of oxide particles and on the desired translucence of the support ceramic and is between 200 and 500 MPa.

The inventive hot-pressing technique is especially advantageous because all undercuts or also the two bridge members which form the slide connection can be precisely connected with one another.

In order to finish the dental crown, in a manner known per se, a ceramic coating can be applied by a known painting technique. This technique, however, is relatively time-consuming.

More effective results with respect to time and aesthetic appearance can be achieved when the exterior shape according to FIG. 10 is molded with a wax material 18 and embedded according to the hot-pressing method (see FIG. 11) so that the resulting hollow spaces can be filled with the ceramic cover material by hot-pressing. When the blanks are not colored so as to match natural dentin, it is favorable when color characteristics, corresponding already to the dentin material of the selected tooth color, are applied to the support structure according to FIG. 9.

The hot-pressing temperature for the hot-pressing method according to FIG. 11 is within a range substantially below the hot-pressing temperature for hot-pressing the support ceramic according to FIG. 9, for example, 100° to 300° C. below this temperature. This ensures that the support structure is not deformed. It is understood that the ceramic cover material can be softer than the support ceramic since it does not comprise zirconium oxide particles. With respect to coloring and translucence the entire range of color possibilities is at disposal so that it is possible to provide whitish-translucent ceramic cover material that matches the natural enamel of the tooth.

It is understood that the thermal expansion coefficients of the ceramic materials must match one another whereby, when using the additional support ceramic in the above disclosed embodiment (FIG. 9), possible deviations of the thermal expansion coefficients between the reinforcement member and the ceramic cover material are reduced at the contacting surfaces since the support ceramic preferably contains oxide particles, i.e., the same material as the reinforcement member. For an oxide contents of 80% the thermal expansion coefficient of the support ceramic is thus substantially identical to the thermal expansion coefficient of the reinforcement member.

According to a modified and simplified method it is suggested to apply the ceramic cover material directly onto the reinforcement member. Surprisingly, this embodiment also results in favorable and fracture-free dental bridges whereby this method can be used especially in connection with shorter dental bridges and crowns.

According to a further modified embodiment the ceramic material of the reinforcement member is comprised of silicon nitride ceramic or boronitride ceramic. It is understood that a ceramic cover material then preferably has a thermal expansion coefficient matching the thermal expansion coefficient of this ceramic material.

When the recesses provided according to FIG. 5 allow the penetration of the support structure material or ceramic cover material, it is preferred to close off the upper and lower surfaces of the slide connection for reasons of stability. Via the connecting ceramic material, these surfaces act as pulling and pressure elements in the manner of a load distribution of a supporting beam and should not be weakened.

FIG. 12 shows the embodiment of the connecting elements or retention parts 38, 40 of the bridge members 20, 22 of the reinforcement member 2. These connecting elements are especially suitable for molars. In this embodiment the bushing 32 is open at the top and closed at the bottom and at the sides so that a U-shaped cross-section results. It is understood that the orientation of the U shape can also be inverted if this is necessary according to dental considerations.

The left portion of FIG. 13 shows the bridge member 20 in a side view whereby the embodiment of the connecting elements (retention parts) is such that with a sintered diamond grinding wheel any location can be ground so that no other drill instruments are needed. The mounting of a bridge member is possible within a very short period of time, for example, within 5 minutes. The central portion of FIG. 13 shows how the grinding wheel 42 extends from below into the retention part 40. The right portion of FIG. 13 shows the bridge member 22 in a view from the top whereby the projections 28 and 30 extend like fingers laterally outwardly so that the grinding wheel 42 can access easily the respective hollow spaces.

FIG. 14 shows a modified embodiment of a dental bridge manufactured according to the inventive method. In this embodiment, a support structure blank is molded from a light-curing plastic material and is introduced, in the manner disclosed above, into the muffle furnace.

The resulting hollow spaces are filled in the furnace by hot-pressing with a support ceramic material so that the support ceramic material covers the reinforcement element. This ceramic material is preferably comprised of 20 to 40% by weight of glass ceramic or feldspar ceramic and 60 to 80% by weight of zirconium oxide filler particles. The mechanical strength of such a mixture is approximately 300 to 600 MPa.

According to FIG. 15 the ceramic support structure is subsequently covered with a ceramic cover material 18 applied either in powder form or by hot-pressing.

FIG. 16 shows two bridge members 20 and 22 for forming a reinforcement member for the incisor area. The bridge members have, as can be seen in FIG. 17, two overlapping pins instead of the bushing/pin combination. FIG. 18 shows in which manner the support structure bridges the teeth 3 for forming an intermediate tooth.

FIG. 19 shows how the support structure is molded whereby preferably the aforementioned method with light-curing plastic material is used which is embedded and after hot-pressing is substituted with the support ceramic material to form the support structure. The support ceramic material is comprised preferably of 70 to 90% by weight of a glass ceramic or feldspar ceramic and of 10 to 30% by weight of zirconium oxide filler particles. The mechanical strength of such a ceramic is in the range of 200 MPa. Due to the high glass ceramic and feldspar ceramic contents all of the important tooth colors are at disposal and the ceramic materials can have the same light translucence values as the natural tooth dentin or tooth enamel so that an optimal aesthetic appearance is ensured.

FIG. 20 shows a section along the line 1—1 of FIG. 19. It is shown that for the incisor area the connecting elements or retention parts 38 extend securely within the dentin and the ceramic cover material, due to the comparatively large surface area of the connection, provides a secure attachment to the ceramic support structure.

FIG. 21 shows an embodiment of a connector which is suitable for manufacturing by the inventive method. Such a connector serves to connect two teeth without intermediate member. FIG. 21 shows the embodiment in a view from behind, from the top, and in cross-section. The connector acts as a reinforcement member 2 for the ceramic support structure 18 shown in FIG. 22 which may have the aforementioned properties and can be applied according to the aforementioned method.

The present invention is, of course, in no way restricted to the specific disclosure of the specification and drawings, but also encompasses any modifications within the scope of the appended claims.

What is claimed is:

1. A method for manufacturing an artificial tooth replacement for at least one tooth, said method comprising the steps of:

constructing a prefabricated ceramic reinforcement member, the core of which closely fits any receiving cavity prepared in a supporting tooth;

forming connecting elements on the ceramic reinforcement member for fastening the artificial tooth replacement to at least one tooth stump of a patient; and covering the ceramic reinforcement member with a ceramic cover material for completing the artificial tooth replacement.

2. A method according to claim 1, wherein the ceramic reinforcement member is comprised of an oxide ceramic and wherein the step of prefabricating includes sintering the oxide ceramic by hot-pressing.

3. A method according to claim 2, wherein the oxide ceramic is comprised of at least 90% of at least one oxide selected from the group consisting of zirconium oxide and aluminum oxide and 0% to 10% of at least one oxide selected from the group consisting of yttrium oxide, calcium oxide, and magnesium oxide.

4. A method according to claim 1, wherein the ceramic material has a lesser hardness than the ceramic reinforcement member, wherein the ceramic cover material is at least partially comprised of feldspar ceramic, wherein the step of covering includes the step of fusing the feldspar ceramic to the ceramic reinforcement member by a ceramic hot-pressing method.

5. A method according to claim 1, wherein the ceramic reinforcement member is comprised of a ceramic selected from the group consisting of silicon nitride, boronitride, and a ceramic having a flexural strength of more than 700 MPa.

6. A method according to claim 1, wherein the step of prefabricating includes the step of presintering the ceramic reinforcement member, preparing, on an enlarged scale relative to an imprint of a tooth stump of a patient, a receiving opening of the reinforcement member for receiving the tooth stump with the aid of a pantograph, and finish-sintering the reinforcement member.

7. A method according to claim 1, wherein the step of prefabricating includes finish-sintering the ceramic reinforcement member and subsequently preparing a receiving opening of the ceramic reinforcement member for receiving a tooth stump with the aid of a copying and grinding machine that senses with one machine tool an imprint of a tooth stump of a patient and grinds with another machine tool the receiving opening accordingly.

8. A method according to claim 1, wherein the step of prefabricating includes the step of preparing the ceramic reinforcement member as an oversized ceramic blank, milling with the aid of a pantograph a receiving opening, having a shape matching a tooth stump of a patient, into the ceramic blank, and finish-sintering the milled ceramic blank.

9. A method according to claim 1, wherein the step of covering includes the steps of firing and hot-pressing a plurality of differently colored meltable ceramics, in the form of raw material, onto the reinforcement member by hot-pressing.

10. A method according to claim 1, further comprising the step of applying a ceramic support structure onto the ceramic reinforcement member, the ceramic support structure comprised at least partially of the same ceramic material as the ceramic reinforcement member, wherein the step of covering the ceramic cover material is selected from the group consisting of glass, zirconium-containing glass, and feldspar.

11. A method according to claim 1, wherein the step of covering the reinforcement member is completely covered with the ceramic cover material and is designed to engage two tooth stumps of a patient to form a dental bridge.

12. A method according to claim 1, wherein the step of covering includes selecting the ceramic cover material to have a thermal expansion coefficient identical to a thermal expansion coefficient of the ceramic reinforcement member comprised of zirconium oxide ceramic.

13. A method according to claim 1, wherein the step of covering includes selecting the ceramic cover material to be comprised of 20% to 40% by weight of a ceramic selected from the group consisting of glass ceramic and feldspar ceramic and 60% to 80% by weight of zirconium oxide.

14. A method according to claim 1, wherein the step of forming includes imparting to a portion of the connecting element, facing a tooth stump of a patient, a shape suitable for grinding with a grinding wheel and providing the connecting element with a claw facing the tooth stump, wherein a surface of the claw facing the tooth stump is ground to form an abutment for the tooth stump.

15. A method according to claim 1, wherein the step of forming includes imparting to a portion of the connecting element, facing a tooth stump of a patient, a shape with multiple fingers suitable for grinding with a grinding wheel.

16. A method according to claim 15, wherein the fingers are arranged so as to diverge.

17. A method according to claim 15, wherein the fingers are arranged in a star-shaped manner.

18. A method according to claim 1, wherein the step of prefabricating includes producing bridge members as parts of the ceramic reinforcement member and a slide connection for slidably connecting the bridge members, wherein the slide connection comprises a pin and a sleeve.

19. A method according to claim 1, wherein the step of prefabricating includes producing bridge members as parts of the ceramic reinforcement member and a slide connection for slidably connecting the bridge members, wherein the slide connection comprises two overlapping pins extending adjacent to one another in a common plane.

20. A method according to claim 1, wherein the ceramic reinforcement member is a connector between two adjacent teeth of a patient, wherein the step of prefabricating includes providing fastening flaps to be positioned at an inwardly facing side of the teeth and providing a constriction in an area between the teeth.

21. A method according to claim 1, further comprising the step of molding onto the reinforcement member a support structure blank of a light-curing plastic material, subsequently embedding the reinforcement member with support structure blank in a mold, and replacing the light-curing plastic material with a support ceramic material to form a ceramic support structure, wherein the step of covering includes hot-pressing the ceramic cover material onto the ceramic support structure.

22. A method according to claim 1, wherein the step of prefabricating includes selecting a metal for the reinforcement member and wherein the step of covering includes applying an opacity-imparting substance.

23. A method according to claim 22, wherein the step of covering further includes painting a ceramic paint onto the opacity-imparting substance in order to produce a desired color of the artificial tooth replacement.

24. A method for manufacturing an artificial tooth replacement for at least one tooth, said method comprising the steps of:

prefabricating a ceramic reinforcement member, wherein the step of prefabricating includes producing bridge members and a slide connection, for slidably connecting the bridge members, as parts of the ceramic reinforcement member;

forming connecting elements on the ceramic reinforcement member for fastening the artificial tooth replacement to at least one tooth stump of a patient; and covering the ceramic reinforcement member with a ceramic cover material for completing the artificial tooth replacement.

25. A method according to claim 24, wherein the slide connection has a force-transmitting portion that is entirely a part of the ceramic reinforcement member.

26. A method for manufacturing an artificial tooth replacement for at least one tooth, said method comprising the steps of:

prefabricating a ceramic reinforcement member;

forming connecting elements on the ceramic reinforcement member for fastening the artificial tooth replacement to at least one tooth stump of a patient;

providing one of the connecting elements with a hole, and covering the ceramic reinforcement member with a ceramic cover material for completing the artificial tooth replacement and filling the hole with the ceramic cover material by hot-pressing.

* * * * *